(12) United States Patent
Pantoja

(10) Patent No.: US 12,350,574 B2
(45) Date of Patent: Jul. 8, 2025

(54) PROVIDING BIOMETRIC ACHIEVEMENT USER INTERFACE SCREENS ASSOCIATED WITH BIOMETRIC GOALS

(71) Applicant: Google LLC, Mountain View, CA (US)

(72) Inventor: Fernando Pantoja, San Francisco, CA (US)

(73) Assignee: GOOGLE LLC, Mountain View, CA (US)

( * ) Notice: Subject to any disclaimer, the term of this patent is extended or adjusted under 35 U.S.C. 154(b) by 0 days.

(21) Appl. No.: 18/397,639

(22) Filed: Dec. 27, 2023

(65) Prior Publication Data

US 2024/0207711 A1 Jun. 27, 2024

Related U.S. Application Data

(63) Continuation of application No. 18/086,202, filed on Dec. 21, 2022, now Pat. No. 11,890,525.

(51) Int. Cl.
G06F 3/048 (2013.01)
A63B 24/00 (2006.01)
(Continued)

(52) U.S. Cl.
CPC ...... *A63B 71/0622* (2013.01); *A63B 24/0062* (2013.01); *G04G 21/025* (2013.01);
(Continued)

(58) Field of Classification Search
CPC ............ A63B 71/0622; A63B 24/0062; A63B 2024/0068; G16H 40/67; G04G 21/025;
(Continued)

(56) References Cited

U.S. PATENT DOCUMENTS 8,533,620 B2   9/2013 Hoffman et al.
11,452,915 B2  9/2022 Devine et al.
(Continued)

OTHER PUBLICATIONS

Fitbit.com, "Fitbit Versa 3 User Manual", chrome-extension://efaidnbmnnnibpcajpcglclefindmkaj/https://help.fitbit.com/manuals/manual_versa_3_en_US.pdf, retrieved on Jun. 25, 2023, 92 pages.
(Continued)

*Primary Examiner* — David Phantana-angkool
(74) *Attorney, Agent, or Firm* — DORITY & MANNING, P.A.

(57) ABSTRACT

A computing device includes a display device, one or more sensors to obtain biometric information of a user associated with the computing device, and one or more processors to execute instructions stored in one or more memories to: determine whether the user completes one or more biometric goals based on the biometric information, and receive data associated with a first user interface screen and data associated with one or more first biometric achievement user interface screens. Each of the first biometric achievement user interface screens include one or more first user interface elements from the first user interface screen and are associated with biometric goals. The first user interface screen forms at least part of a home screen, and in response to the user completing a first biometric goal, a corresponding first biometric achievement user interface screen associated with completion of the first biometric goal is provided.

20 Claims, 8 Drawing Sheets

(51) Int. Cl.
  *A63B 71/06* (2006.01)
  *G04G 21/02* (2010.01)
  *G04G 99/00* (2010.01)
  *G06F 3/01* (2006.01)
  *G06F 3/0481* (2022.01)
  *G06F 3/04842* (2022.01)
  *G16H 40/67* (2018.01)

(52) U.S. Cl.
  CPC ........... *G04G 99/006* (2013.01); *G06F 3/011* (2013.01); *G06F 3/0481* (2013.01); *G06F 3/04842* (2013.01); *G16H 40/67* (2018.01); *A63B 2024/0068* (2013.01); *A63B 2071/0625* (2013.01); *A63B 2071/0655* (2013.01)

(58) Field of Classification Search
  CPC ..... G04G 99/006; G06F 3/011; G06F 3/0481; G06F 3/04842
  See application file for complete search history.

(56) References Cited

U.S. PATENT DOCUMENTS

| | | | |
|---|---|---|---|
| 11,928,947 B2* | 3/2024 | Jiang | .................... G08B 21/043 |
| 2011/0197157 A1 | 8/2011 | Hoffman et al. | |
| 2017/0053542 A1 | 2/2017 | Wilson et al. | |
| 2018/0259913 A1 | 9/2018 | Brown et al. | |
| 2018/0345078 A1 | 12/2018 | Blahnik et al. | |
| 2019/0365228 A1 | 12/2019 | Rondoni et al. | |
| 2020/0033952 A1 | 1/2020 | Pantelopoulos et al. | |
| 2020/0381099 A1 | 12/2020 | Crowley et al. | |
| 2020/0382613 A1 | 12/2020 | Sundstrom et al. | |
| 2021/0042028 A1 | 2/2021 | Block et al. | |
| 2021/0098110 A1* | 4/2021 | Periyasamy | ........... G16H 20/70 |
| 2021/0153805 A1 | 5/2021 | Carpenter et al. | |
| 2021/0183511 A1 | 6/2021 | Orenstein et al. | |
| 2021/0255826 A1 | 8/2021 | Devine et al. | |
| 2022/0357823 A1 | 11/2022 | Choi | |
| 2022/0392589 A1* | 12/2022 | Lauritzen | ........... G06F 3/04817 |
| 2023/0114054 A1 | 4/2023 | Crowley et al. | |
| 2023/0389861 A1* | 12/2023 | Felton | .................... G16H 30/20 |
| 2023/0393616 A1* | 12/2023 | Chao | ...................... G06F 3/017 |
| 2024/0005432 A1* | 1/2024 | Aman | .................... G16H 10/40 |
| 2024/0161888 A1* | 5/2024 | Crowley | ................. G16H 50/70 |

OTHER PUBLICATIONS

Fitbit.com, "Create Your Own Fireworks Display This 4th of July", Jul. 2, 2019, https://web.archive.org/ web/20220519182131/https:/ blog.fitbit.com/fireworks/, retrieved on Jun. 25, 2023, 3 pages.
International Search Report and Written Opinion for PCT/US2023/ 084101, mailed on Apr. 15, 2024, 11 pages.

* cited by examiner

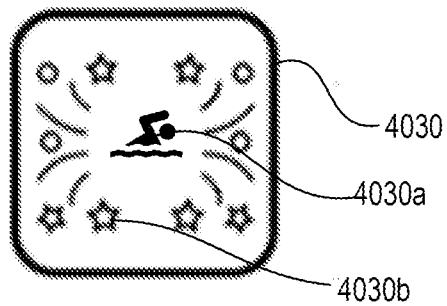
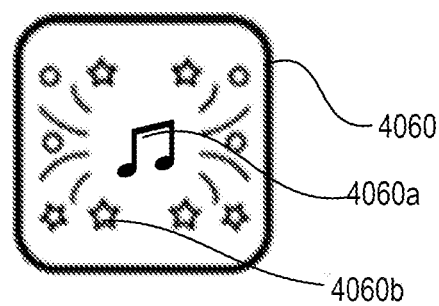
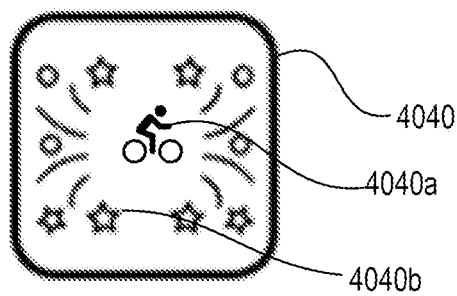
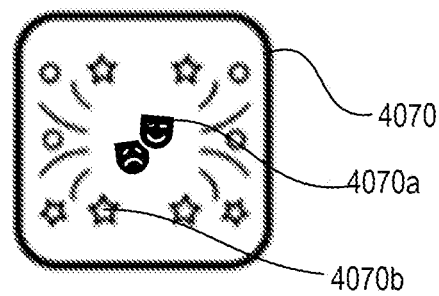
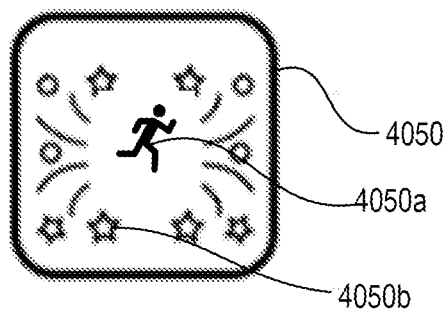
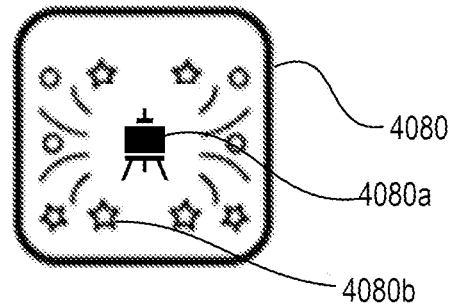
FIG. 4B
FIG. 4C

PROVIDING BIOMETRIC ACHIEVEMENT USER INTERFACE SCREENS ASSOCIATED WITH BIOMETRIC GOALS

PRIORITY CLAIM

This application is a continuation of U.S. application Ser. No. 18/086,202 having a filing date of Dec. 21, 2022, which is incorporated by reference herein in its entirety for all purposes.

FIELD

The disclosure relates generally to computing devices that can be used to measure biometric information of a user. More particularly, the disclosure relates to computing devices which measure biometric information of the user while the user engages in an activity, for example, running, walking, swimming, cycling, and the like, and provides a biometric achievement user interface screen when the user accomplishes a biometric goal relating to the activity.

BACKGROUND

Some computing devices, such as a fitness watch, are capable of measuring human biometric information of the user. Some computing devices provide feedback to the user which includes metrics relating an activity the user engages in (e.g., a number of steps walked). However, biometric achievement user interface screens are generally provided as part of system-level updates relating to the computing device and are not related to a home screen of the computing device.

SUMMARY

Aspects and advantages of embodiments of the disclosure will be set forth in part in the following description, or can be learned from the description, or can be learned through practice of the example embodiments.

In an example embodiment, a computing device (e.g., a smartphone, a smartwatch, a tablet, etc.), is provided. The computing device includes a display device, one or more sensors configured to obtain biometric information of a user associated with the computing device, one or more memories configured to store instructions, and one or more processors configured to execute the instructions stored in the one or more memories to: determine whether the user completes one or more biometric goals based on the biometric information obtained by the one or more sensors, and receive, in response to a selection of a first user interface screen among a plurality of user interface screens, data associated with the first user interface screen and data associated with one or more first biometric achievement user interface screens. Each of the one or more first biometric achievement user interface screens include one or more first user interface elements from the first user interface screen and each of the one or more first biometric achievement user interface screens are associated with respective biometric goals among the one or more biometric goals. The one or more processors are also configured to execute the instructions stored in the one or more memories to: provide, for presentation on the display device, the first user interface screen as at least part of a home screen of the computing device, and in response to the user completing a first biometric goal among the one or more biometric goals, provide, for presentation on the display device, a corresponding first biometric achievement user interface screen associated with completion of the first biometric goal.

In some implementations, the selection of the first user interface screen among the plurality of user interface screens is received at an external computing device, and the one or more processors are configured to receive the data associated with the first user interface screen and the data associated with the one or more first biometric achievement user interface screens from a server computing system, in response to the selection of the first user interface screen at the external computing device.

In some implementations, each of the one or more first biometric achievement user interface screens include different user interface elements from the first user interface screen to denote respective biometric goals among the one or more biometric goals.

In some implementations, the computing device is a wearable computing device, and the first user interface screen corresponds to a watch face which is displayed on the home screen.

In some implementations, in response to the user completing the first biometric goal among the one or more biometric goals, the one or more processors are configured to execute the instructions stored in the one or more memories to provide at least one of haptic feedback associated with the first biometric goal or an audio output associated with the first biometric goal.

In some implementations, the one or more processors are configured to receive, in response to a selection of a second user interface screen among the plurality of user interface screens, data associated with the second user interface screen and data associated with one or more second biometric achievement user interface screens, wherein each of the one or more second biometric achievement user interface screens include one or more second user interface elements from the second user interface screen and each of the one or more second biometric achievement user interface screens are associated with respective biometric goals among the one or more biometric goals.

In some implementations, the computing device further comprises an activity detector configured to provide an output indicating an activity the user is performing among a plurality of activities. In some implementations, the first user interface screen is associated with a first activity among the plurality of activities, the second user interface screen is associated with a second activity among the plurality of activities, and the one or more processors are configured to execute the instructions stored in the one or more memories to switch from providing, for presentation on the display device, the first user interface screen as at least part of the home screen to providing, for presentation on the display device, the second user interface screen as at least part of the home screen, in response to the output provided by the activity detector indicating the user has changed from performing the first activity to performing the second activity In some implementations, the plurality of activities include two or more of walking, running, swimming, cycling, climbing, weightlifting, nutritional, or sleeping.

In some implementations, the first user interface screen is associated with a first activity among a plurality of activities, the first biometric goal relates to the first activity, the one or more first biometric achievement user interface screens are associated with achieving one or more thresholds toward the completion of the first biometric goal relating to the first activity, and the corresponding biometric achievement user interface screen is associated with the completion of the first biometric goal relating to the first activity.

In some implementations, the one or more first user interface elements correspond to graphical images, and the one or more processors are configured to execute the instructions stored in the one or more memories to limit an area which each of the first biometric achievement user interface screens encompass on the display device to less than a threshold size.

In some implementations, the one or more processors are configured to execute the instructions stored in the one or more memories to provide an animation including the one or more first user interface elements, via one or more of the first biometric achievement user interface screens, and to limit a duration of time which the animation plays to less than a threshold duration of time.

In some implementations, before receiving the data associated with the corresponding biometric achievement user interface screen, the one or more processors are configured to execute the instructions stored in the one or more memories to provide, for presentation on the display device, a default biometric achievement user interface screen associated with the completion of the first biometric goal, data associated with the default biometric achievement user interface screen being stored in the one or more memories, and in response to receiving the data associated with the corresponding biometric achievement user interface screen, the one or more processors are configured to execute the instructions stored in the one or more memories to stop providing, for presentation on the display device, the default biometric achievement user interface screen associated with the completion of the first biometric goal.

In some implementations, before receiving the data associated with the corresponding biometric achievement user interface screen, the one or more processors are configured to execute the instructions stored in the one or more memories to provide, for presentation on the display device, a default biometric achievement user interface screen associated with the completion of the first biometric goal, data associated with the default biometric achievement user interface screen being stored in the one or more memories, and in response to receiving the data associated with the corresponding biometric achievement user interface screen, the one or more processors are configured to execute the instructions stored in the one or more memories to delete the data associated with the default biometric achievement user interface screen or to overwrite the data associated with the default biometric achievement user interface screen with the data associated with the corresponding biometric achievement user interface screen.

In some implementations, the first user interface screen is associated with a first activity among a plurality of activities, the first biometric goal relates to the first activity, before receiving the data associated with the one or more first biometric achievement user interface screens, the first biometric goal relating to the first activity is unmapped to any biometric achievement user interface screen, in response to receiving the data associated with the corresponding biometric achievement user interface screen, the one or more processors are configured to execute the instructions stored in the one or more memories to map the corresponding biometric achievement user interface screen to the first biometric goal to associate the corresponding biometric achievement user interface screen with the completion of the first biometric goal, and in response to the user completing the first biometric goal relating to the first activity the one or more processors are configured to execute the instructions stored in the one or more memories to provide, for presentation on the display device, the corresponding biometric achievement user interface screen associated with the completion of the first biometric goal.

In an example embodiment, a computer-implemented method is provided. The computer-implemented method includes obtaining, by one or more sensors, biometric information of a user associated with a computing device comprising one or more processors; determining, by the computing device, whether the user completes one or more biometric goals based on the biometric information obtained by the one or more sensors; receiving, in response to a selection of a first user interface screen among a plurality of user interface screens, data associated with the first user interface screen and data associated with one or more first biometric achievement user interface screens, wherein each of the one or more first biometric achievement user interface screens include one or more first user interface elements from the first user interface screen and each of the one or more first biometric achievement user interface screens are associated with respective biometric goals among the one or more biometric goals; providing, for presentation on a display device of the computing device, the first user interface screen as at least part of a home screen of the computing device; and in response to the user completing a first biometric goal among the one or more biometric goals, providing, for presentation on the display device, a corresponding first biometric achievement user interface screen associated with completion of the first biometric goal.

In some implementations, each of the one or more first biometric achievement user interface screens include different user interface elements from the first user interface screen to denote respective biometric goals among the one or more biometric goals.

In some implementations, the method includes providing, by an activity detector, an output indicating an activity the user is performing among a plurality of activities, the plurality of activities including a first activity associated with the first user interface screen and a second activity associated with a second user interface screen, switching from providing, for presentation on the display device, the first user interface screen as at least part of the home screen to providing, for presentation on the display device, the second user interface screen as at least part of the home screen, in response to the output provided by the activity detector indicating the user has changed from performing the first activity to performing the second activity.

In an example embodiment, a non-transitory computer-readable medium which stores instructions that are executable by one or more processors of a computing device is provided. The non-transitory computer-readable medium stores instructions which are executable by one or more processors of a computing device. The instructions include: instructions to cause the one or more processors to obtain biometric information of a user associated with the computing device; instructions to cause the one or more processors to determine whether the user completes one or more biometric goals based on the biometric information; instructions to cause the one or more processors to receive, in response to a selection of a first user interface screen among a plurality of user interface screens, data associated with the first user interface screen and data associated with one or more first biometric achievement user interface screens, wherein each of the one or more first biometric achievement user interface screens include one or more first user interface elements from the first user interface screen and each of the one or more first biometric achievement user interface screens are associated with respective biometric goals among the one or more biometric goals; instructions to cause the one or more processors to provide, for presentation on a display device of the computing device, the first user interface screen as at least part of a home screen of the computing device; and instructions to cause the one or more processors to provide, for presentation on the display device, a corresponding first biometric achievement user interface screen associated with completion of a first biometric goal among the one or more biometric goals, in response to the user completing the first biometric goal.

In some implementations, the non-transitory computer-readable medium may store additional instructions. For example, before receiving the data associated with the corresponding biometric achievement user interface screen, the instructions comprise instructions to cause the one or more processors to provide, for presentation on the display device, a default biometric achievement user interface screen associated with the completion of the first biometric goal, data associated with the default biometric achievement user interface screen being stored in the non-transitory computer-readable medium, and in response to receiving the data associated with the corresponding biometric achievement user interface screen, the instructions comprise instructions to cause the one or more processors to delete the data associated with the default biometric achievement user interface screen or to overwrite the data associated with the default biometric achievement user interface screen with the data associated with the corresponding biometric achievement user interface screen In some implementations, the first user interface screen is associated with a first activity among a plurality of activities, the first biometric goal relates to the first activity, before receiving the data associated with the one or more first biometric achievement user interface screens, the first biometric goal relating to the first activity is unmapped to any biometric achievement user interface screen, in response to receiving the data associated with the corresponding biometric achievement user interface screen, the instructions comprise instructions to cause the one or more processors to map the corresponding biometric achievement user interface screen to the first biometric goal to associate the corresponding biometric achievement user interface screen with the completion of the first biometric goal, and in response to the user completing the first biometric goal relating to the first activity the instructions comprise instructions to cause the one or more processors to provide, for presentation on the display device, the corresponding biometric achievement user interface screen associated with the completion of the first biometric goal.

The non-transitory computer-readable medium may store additional instructions to execute other aspects and operations of the computing device and computer-implemented method as described herein.

These and other features, aspects, and advantages of various embodiments of the disclosure will become better understood with reference to the following description, drawings, and appended claims. The accompanying drawings, which are incorporated in and constitute a part of this specification, illustrate examples of the disclosure and, together with the description, serve to explain the related principles.

BRIEF DESCRIPTION OF THE DRAWINGS

Detailed discussion of example embodiments directed to one of ordinary skill in the art is set forth in the specification, which makes reference to the appended drawings, in which:

FIGS. 4B through 4C are example illustrations of various biometric achievement user interface screens which can be selected for presentation on a computing device, according to one or more examples of the disclosure;

DETAILED DESCRIPTION

Figure 1:
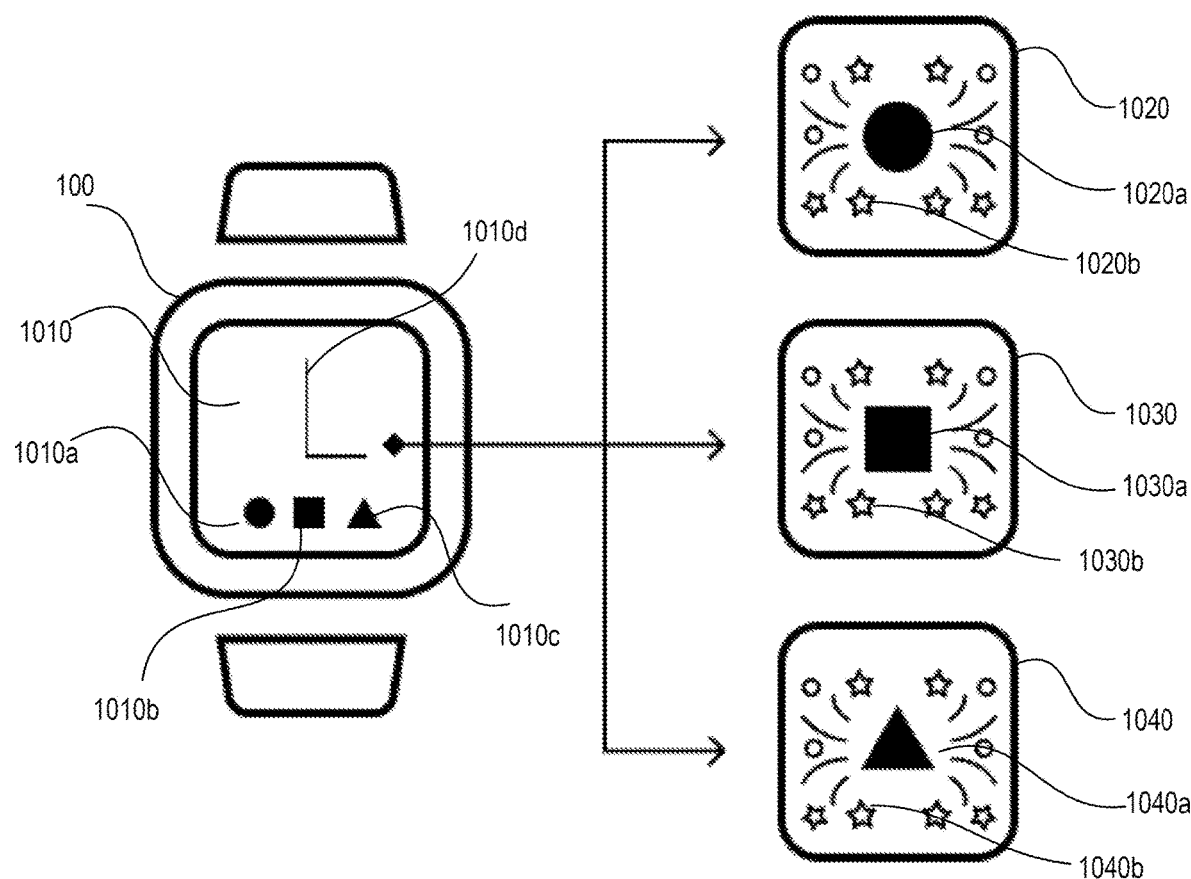
FIG. 1 is an example illustration of a user interface screen of a computing device and various biometric achievement user interface screens, according to one or more examples of the disclosure.

Reference now will be made to embodiments of the disclosure, one or more examples of which are illustrated in the drawings. Each example is provided by way of explanation of the disclosure and is not intended to limit the disclosure. In fact, it will be apparent to those skilled in the art that various modifications and variations can be made to the disclosure without departing from the scope or spirit of the disclosure. For instance, features illustrated or described as part of one embodiment can be used with another embodiment to yield a still further embodiment. Thus, it is intended that the disclosure covers such modifications and variations as come within the scope of the appended claims and their equivalents.

Terms used herein are used to describe the example embodiments and are not intended to limit and/or restrict the disclosure. The singular forms "a," "an" and "the" are intended to include the plural forms as well, unless the context clearly indicates otherwise. In this disclosure, terms such as "including", "having", "comprising", and the like are used to specify features, numbers, steps, operations, elements, components, or combinations thereof, but do not preclude the presence or addition of one or more of the features, elements, steps, operations, elements, components, or combinations thereof.

It will be understood that, although the terms first, second, third, etc., may be used herein to describe various elements, the elements are not limited by these terms. Instead, these terms are used to distinguish one element from another element. For example, without departing from the scope of the disclosure, a first element may be termed as a second element, and a second element may be termed as a first element.

The term "and/or" includes a combination of a plurality of related listed items or any item of the plurality of related listed items. For example, the scope of the expression or phrase "A and/or B" includes the item "A", the item "B", and the combination of items "A and B".

In addition, the scope of the expression or phrase "at least one of A or B" is intended to include all of the following: (1) at least one of A, (2) at least one of B, and (3) at least one of A and at least one of B. Likewise, the scope of the expression or phrase "at least one of A, B, or C" is intended to include all of the following: (1) at least one of A, (2) at least one of B, (3) at least one of C, (4) at least one of A and at least one of B, (5) at least one of A and at least one of C, (6) at least one of B and at least one of C, and (7) at least one of A, at least one of B, and at least one of C.

Example aspects of the disclosure are directed to a computing device, for example, a smartphone, a smartwatch, a tablet, biometric tracker device, etc. that can be used to measure biometric information of a user. For example, the computing device may be configured to measure biometric information of the user when the computing device is carried or worn by the user while the user engages in an activity, for example, running, walking, swimming, cycling, etc. For example, the computing device may be configured to provide a biometric achievement user interface screen when the user accomplishes a biometric goal relating to the activity. For example, the biometric achievement user interface screen may include elements or components (e.g., graphical images, icons, etc.) from a user interface screen that serves as at least part of a home screen for the computing device (e.g., a clock face).

Examples aspects of the disclosure are directed to a biometric measurement application which is configured to track or monitor biometric information associated with a user, for example, based on information received from various sensors. For example, the biometric measurement application may be configured to track or monitor biometric information associated with the user while the user engages in various activities. The activities may include one or more of walking, running, swimming, cycling, climbing, weightlifting, sleeping, and the like. The biometric measurement application may be configured to set or establish various default biometric goals which are associated with the activities. An example goal may include for the user to walk 10,000 steps in one day to complete a goal associated with the activity of walking. Intermediate goals may correspond to threshold values which can be met or satisfied by the user engaging in the activity in an effort to progress toward completing the goal. Example threshold values in relation to the goal of walking 10,000 steps in one day may include 2,500 steps, 5,000 steps, and 7,500 steps. However, these values are merely example values and other threshold or intermediate values could be used. In some implementations, the user can define or customize various biometric goals and/or threshold values which correspond to intermediate biometric goals.

For example, the computing device may be configured to track the progress of a user as the user engages in an activity and determine whether the user completes a biometric goal (e.g., walking a certain number of steps, cycling a certain number of miles, swimming a certain number of laps, sleeping a certain number of hours, etc.).

For example, the user may define or select one or more goals associated with the activity through the biometric measurement application (or the biometric measurement application may have one or more default biometric goals associated with the activity). When the user achieves a goal, a celebration may be displayed on a display screen or user interface screen of the computing device. In some implementations, an intermediate celebration (or micro-celebration) may be displayed on the display screen or user interface screen of the computing device at one or more predetermined points before the biometric goal is actually achieved which correspond to the threshold values (intermediate goals) described above. Different celebrations may also be shown according to a type of activity. The celebrations may include a graphical image that is displayed and intended to encourage the user with respect to achieving their biometric goal which is associated with the activity. The celebrations may include an animation including a series of graphical images that are displayed and intended to encourage the user with respect to achieving their biometric goal which is associated with the activity. Haptic feedback and/or audio output may also be provided in relation to completing a biometric goal and/or achieving an intermediate biometric goal.

According to examples of the disclosure, users of the computing device can select a user interface screen from a plurality of user interface screens which serves as a home screen (i.e., a main menu, a home page, a startup screen, etc.) or as at least part of the home screen. For example, the user interface screen may be in the form of a clock face.

In some implementations, the user can select, via the biometric measurement application at the computing device, the user interface screen from a plurality of user interface screens which are stored remotely, for example, at a server computing system. In response to the user selecting the user interface screen at the computing device, a request can then be transmitted from the computing device to the server computing system. In response to the server computing system receiving the request from the computing device, the server computing system can transmit data associated with the user interface screen to the computing device. Furthermore, the server computing system can automatically transmit data associated with one or more biometric achievement user interface screens to the computing device. For example, each of the one or more biometric achievement user interface screens may include one or more user interface elements from the selected user interface screen and each of the one or more biometric achievement user interface screens may be associated with various biometric goals.

For example, a first biometric achievement user interface screen may be associated with an intermediate biometric goal relating to an activity (e.g., walking 3,000 steps), a second biometric achievement user interface screen may be associated with another intermediate biometric goal relating to the activity (e.g., walking 6,000 steps), and a third biometric achievement user interface screen may be associated with the completion of the biometric goal relating to the activity (e.g., walking 10,000 steps). In some implementations, each of the biometric achievement user interface screens may include different user interface elements from the user interface screen to denote different biometric goals. For example, the user interface screen may include a geometric design having a circle-shaped user interface element, a square-shaped user interface element, and a triangle-shaped user interface element. For example, the first biometric achievement user interface screen may include the circle-shaped user interface element, the second biometric achievement user interface screen may include the square-shaped user interface element, and the third biometric achievement user interface screen may include the triangle-shaped user interface element.

For example, a first biometric achievement user interface screen may be associated with a biometric goal relating to a first activity (e.g., walking 10,000 steps), a second biometric achievement user interface screen may be associated with a biometric goal relating to a second activity (e.g., swimming 20 laps), and a third biometric achievement user interface screen may be associated with a biometric goal relating to a third activity (e.g., cycling 10 miles). In some implementations, each of the biometric achievement user interface screens may include different user interface elements from the user interface screen to denote different biometric goals. For example, the user interface screen may include a geometric design having a circle-shaped user interface element, a square-shaped user interface element, and a triangle-shaped user interface element. For example, the first biometric achievement user interface screen may include the circle-shaped user interface element, the second biometric achievement user interface screen may include the square-shaped user interface element, and the third biometric achievement user interface screen may include the triangle-shaped user interface element.

In some implementations, the user can select, via a biometric measurement application at an external computing device, the user interface screen from a plurality of user interface screens which are stored locally on the external computing device. In response to the user selecting the user interface screen at the external computing device, the external computing device can transmit data associated with the user interface screen to the computing device. Furthermore, the external computing device can automatically transmit data associated with one or more biometric achievement user interface screens to the computing device. For example, each of the one or more biometric achievement user interface screens may include one or more user interface elements from the selected user interface screen and each of the one or more biometric achievement user interface screens may be associated with various biometric goals, as already discussed above. For example, the external computing device may be a smartphone and the computing device may be a smartwatch.

In some implementations, the user can select, via the biometric measurement application at the external computing device, the user interface screen from a plurality of user interface screens which are stored remotely, for example, at the server computing system. In response to the user selecting the user interface screen at the external computing device, a request can then be transmitted from the external computing device to the server computing system. In response to the server computing system receiving the request from the external computing device, the server computing system can transmit data associated with the user interface screen and data associated with one or more biometric achievement user interface screens to the external computing device which then transmits the data associated with the user interface screen to the computing device, or the server computing system can transmit the data associated with the user interface screen to the computing device. Furthermore, the server computing system can automatically transmit data associated with one or more biometric achievement user interface screens to the external computing device which then transmits the data associated with the one or more biometric achievement user interface screens to the computing device, or the server computing system can transmit the data associated with the one or more biometric achievement user interface screens to the computing device. For example, each of the one or more biometric achievement user interface screens may include one or more user interface elements from the selected user interface screen and each of the one or more biometric achievement user interface screens may be associated with various biometric goals, as already discussed above. For example, the external computing device may be a smartphone and the computing device may be a smartwatch.

Therefore, according to examples described herein the user does not specifically select the biometric achievement user interface screens, but instead selects a main or general user interface screen from which the biometric achievement user interface screens are derived. Accordingly, a number of interactions required of the user is reduced and network resources are conserved by the automatic transmission of the data associated with the one or more biometric achievement user interface screens, rather than a user navigating through various menus or applications to select specific biometric achievement user interface screens.

In some implementations, the user may select a second user interface screen from among the plurality of user interface screens. For example, the first user interface screen may be associated with a first type of activity (e.g., swimming), and the second user interface screen may be associated with a second type of activity (e.g., bicycling).

In some implementations, an activity detector may be configured to detect or determine a type of activity a user is engaged in. For example, if an output provided by the activity detector indicates the user is engaged in swimming, the first user interface screen may be provided as at least part of the home screen. For example, if an output provided by the activity detector indicates the user is engaged in bicycling, the second user interface screen may be provided as at least part of the home screen. For example, the computing device may automatically change or switch the user interface screen from the first user interface screen to the second user interface screen in response to the output of the activity detector indicating the user has switched from one activity to another (e.g., from swimming to bicycling). In association with changing the user interface screens, corresponding biometric achievement user interface screens are also provided in connection with the different activities engaged in by the user.

For example, the computing device may not be programmed or configured to provide a celebratory biometric achievement user interface screen in relation to biometric goals associated with a particular activity. According to examples of the disclosure, when a user selects a user interface screen and the computing device receives data associated with the selected user interface screen and data associated with one or more first biometric achievement user interface screens, the computing device may be configured to automatically map or assign one or more of the first biometric achievement user interface screens to the biometric goals associated with the particular activity. In some implementations, the user may identify activities to which the selected user interface screen should be mapped, for example, via the biometric measurement application.

For example, the computing device may be programmed or configured to provide a default biometric achievement user interface screen in relation to celebrating biometric goals associated with a particular activity. According to examples of the disclosure, when a user selects a user interface screen and the computing device receives data associated with the selected user interface screen and data associated with one or more first biometric achievement user interface screens, the computing device may be configured to automatically suppress or stop providing for presentation on the display device the default biometric achievement user interface screen associated with completing the first biometric goal. Further, in response to the user selecting the user interface screen and the computing device receiving the data associated with the selected user interface screen and the data associated with the one or more first biometric achievement user interface screens, the computing device may be configured to automatically provide for presentation on the display device one or more of the first biometric achievement user interface screens to celebrate the completion of various biometric goals associated with the particular activity.

For example, the computing device may be programmed or configured to provide a default biometric achievement user interface screen in relation to celebrating biometric goals associated with a particular activity. In some implementations, when a user selects a user interface screen and the computing device receives data associated with the selected user interface screen and data associated with one or more first biometric achievement user interface screens, the computing device may be configured to delete the data associated with the default biometric achievement user interface screen. In some implementations, when a user selects a user interface screen and the computing device receives data associated with the selected user interface screen and data associated with one or more first biometric achievement user interface screens, the computing device may be configured to overwrite the data associated with the default biometric achievement user interface screen with the data associated with the corresponding biometric achievement user interface screen. Deleting or overwriting the data associated with the default biometric achievement user interface screen may conserve computing resources of the computing device, for example, storage resources. In some implementations, the default biometric achievement user interface screen may correspond to a previously received biometric achievement user interface screen rather than a biometric achievement user interface screen which is stored on the computing device, for example, by the manufacturer or when first powering on or initializing the computing device. Further, in response to the user selecting the user interface screen and the computing device receiving the data associated with the selected user interface screen and the data associated with the one or more first biometric achievement user interface screens, the computing device may be configured to automatically provide for presentation on the display device one or more of the first biometric achievement user interface screens to celebrate the completion of various biometric goals associated with the particular activity.

In some implementations, the biometric measurement application may limit a physical area which a biometric achievement user interface screen encompasses on the display device, for example, to save power of the computing device (e.g., for powering the display of the display device). The biometric measurement application may limit the physical area of the biometric achievement user interface screen to a threshold area value (e.g., ¼ of an area of the displayable surface of the display device, ½ of an area of the displayable surface of the display device, ⅔ of an area of the displayable surface of the display device, etc.).

In some implementations, the biometric measurement application may additionally, or alternatively, limit a duration for which the biometric achievement user interface screen is shown on the display device, for example, to save power of the computing device (e.g., for powering the display of the display device). The biometric measurement application may limit the duration of time the biometric achievement user interface screen is shown to a threshold time value (e.g., less than 5 seconds, less than 3 seconds, less than 2 seconds, etc.). For example, the biometric achievement user interface screen may include an animation which celebrates the completion of a biometric goal or an intermediate biometric goal. The biometric measurement application may also limit the duration of time the animation is shown to a threshold time value (e.g., less than 5 seconds, less than 3 seconds, less than 2 seconds, etc.).

Example aspects of the disclosure provide several technical effects, benefits, and/or improvements in computing technology and the technology of computing devices and health or biometric monitoring devices. According to some current methods, computing devices may receive or update biometric achievement user interface screens when a system-level update occurs with respect to the computing device (e.g., a firmware update). Internal processes for implementing a system-level update are complex and time consuming. In contrast, according to the examples of the disclosure, various user interface screens (e.g., clock faces) may be designed and offered for selection by users where data associated with biometric achievement user interface screens which celebrate biometric accomplishments of the user can be provided automatically in conjunction with the selection of the user interface screen by the user. Thus, the examples of the disclosure do not rely on a system-level update of the computing device for changing a celebratory experience for the user, but can be selected at any time by the user via selection of a user interface screen which includes elements utilized by the biometric achievement user interface screens. Such a process can further efficiently use network resources by transmitting data associated with a user interface screen at a same time (or substantially the same time) as transmitting data associated with biometric achievement user interface screens.

For example, according to one or more examples of the disclosure, in response to receiving data which is associated with a user interface screen (e.g., a clock face), data associated with celebrations is also received by the computing device. By delaying the reception of the data associated with celebrations until a time at which the user selects a user interface screen (e.g., the clock face), storage space on the computing device can be saved. In addition, by receiving data associated with celebrations at a time that data associated with the user interface screen (e.g., the clock face) is downloaded, it can be ensured that the data associated with celebrations is received, as network connectivity at a later time may not be available or may be degraded. Furthermore, automatically receiving data associated with celebrations at a time that data associated with the user interface screen is received in response to a user selecting a user interface screen, reduces the number of interactions with a user, saving computing resources. For example, the user need not select various biometric achievement user interface screens and need not make a separate request for the data associated with the various biometric achievement user interface screens to be transmitted to the computing device.

Referring now to the drawings, FIG. 1 illustrates an example illustration of a user interface screen of a computing device and various biometric achievement user interface screens, according to one or more examples of the disclosure. In FIG. 1, a computing device 100 (e.g., a smartwatch as shown in the drawing) includes a user interface screen 1010 in the form of a watch face. The computing device 100 can also include other electronic devices including a smartphone, a tablet, etc. The user interface screen 1010 may include various user interface elements, including first user interface element 1010a which is circle-shaped, second user interface element 1010b which is square-shaped, third user interface element 1010c which is triangle-shaped, and clock hands 1010d which can be used to indicate a time of day.

As described herein, the user interface screen 1010 may serve as a home screen or as at least part of a home screen of the computing device 100. A home screen may include a main menu, a home page, a startup screen, and the like. As described herein, the computing device 100 may be configured so that the user interface screen 1010 may be changeable or customizable. That is, a user associated with the computing device 100 may select a user interface screen from among a plurality of user interface screens which can be used as at least part of the home screen. The user interface screen 1010 may have features which are of interest to the user and improve the user experience with the computing device 100. For example, user interface screen 1010 includes user interface elements having various geometric shape.

For example, the computing device 100 may be configured to measure biometric information of the user. For example, the computing device 100 may measure biometric information of the user when the computing device is carried or worn by the user while the user engages in an activity, for example, running, walking, swimming, cycling, sleeping, etc. For example, the computing device 100 may be configured to provide a biometric achievement user interface screen when the user accomplishes a biometric goal relating to the activity. For example, the biometric achievement user interface screen may include elements or components (e.g., graphical images, icons, etc.) from the user interface screen 1010 that serves as at least part of the home screen for the computing device 100.

Referring to FIG. 1, three biometric achievement user interface screens are illustrated. For example, FIG. 1 illustrates a first biometric achievement user interface screen 1020, a second biometric achievement user interface screen 1030, and a third biometric achievement user interface screen 1040. As shown in FIG. 1, each of the biometric achievement user interface screens may include one or more user interface elements that are the same as or are derived from the user interface screen 1010. For example, each of the biometric achievement user interface screens may include a different user interface element from each other (e.g., a circle-shaped user interface element 1020a in first biometric achievement user interface screen 1020, a square-shaped user interface element 1030a in second biometric achievement user interface screen 1030, and a triangle-shaped user interface element 1040a in third biometric achievement user interface screen 1040). For example, each of the biometric achievement user interface screens may include other user interface elements that are not derived from the user interface screen 1010. The other user interface elements that are not derived from the user interface screen 1010 may be the same for each of the biometric achievement user interface screens or may be different from each other. For example, in FIG. 1, each of the biometric achievement user interface screens 1020, 1030, and 1040 include common user interface elements 1020b, 1030b, and 1040b (e.g., a celebratory display including stars, hollow circles, and curved lines). The user interface elements provided for the biometric achievement user interface screens may include graphical images, icons, symbols, and the like.

For example, the biometric achievement user interface screens may include static elements or dynamic elements. That is, one or more of the user interface elements provided in a biometric achievement user interface screen may remain stationary or may move. For example, the biometric achievement user interface screen may include one or more user interface elements which are part of an animation which celebrates the completion of a biometric goal or an intermediate biometric goal. For example, the celebration may include an animation including a series of graphical images that are displayed and intended to encourage the user with respect to achieving a biometric goal which is associated with an activity a user engages in.

Figure 2:
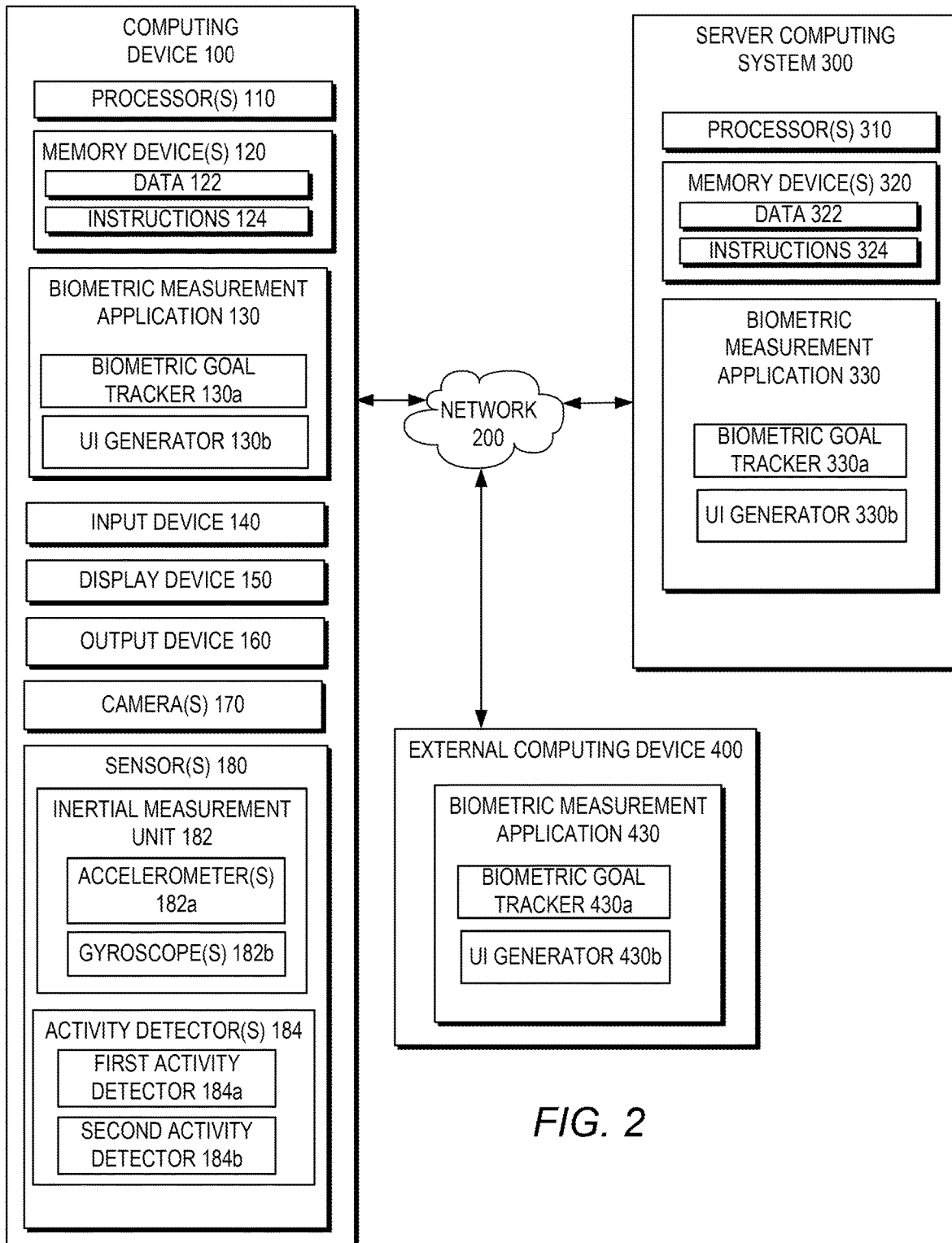
FIG. 2 is an example system including block diagrams of a computing device, an external computing device, and a server computing system, according to one or more examples of the disclosure.

Referring to the drawings, FIG. 2 illustrates an example system including block diagrams of a computing device, an external computing device, and a server computing system, according to one or more examples of the disclosure. In FIG. 1, the example system includes a computing device 100, a server computing system 300, and an external computing device 400, which are connected with one another over a network 200. Any communications interfaces suitable for communicating via the network 200 (such as a network interface card) may be utilized as appropriate or desired by the computing device 100 and one or more external computing devices 400.

The external computing device 400 may include a personal computer, a smartphone, a laptop, a tablet computer, and the like. The server computing system 300 can include a server, or a combination of servers (e.g., a web server, application server, etc.) in communication with one another, for example in a distributed fashion.

According to some implementations of the disclosure, the computing device 100 may communicate with the external computing device 400 and/or server computing system 300 to share biometric information of the user (e.g., to store the biometric information in a database of the server computing system 300, a medical service provider, a laptop, etc.).

According to some implementations of the disclosure, the computing device 100, server computing system 300, and the external computing device 400 may communicate with each other via a biometric measurement application. The biometric measurement application may be configured to enable a user to set or define biometric goals with respect to an activity that the user is to engage in, for example. The biometric measurement application may be configured to enable a user to select a user interface screen from among a plurality of user interface screens which is displayable on the display device 150 of the computing device 100. The biometric measurement application may be configured to provide, in response to the selection of the user interface screen, data associated with the user interface screen, as well as data associated with one or more biometric achievement user interface screens. That is, in conjunction with receiving data associated with the user interface screen (in response to the selection of the user interface screen), the computing device 100 also receives data associated with one or more biometric achievement user interface screens, as described in more detail below.

The network 200 may include any type of communications network such as a local area network (LAN), wireless local area network (WLAN), wide area network (WAN), personal area network (PAN), virtual private network (VPN), or the like. For example, wireless communication between elements of the examples described herein may be performed via a wireless LAN, Wi-Fi, Bluetooth, ZigBee, Wi-Fi direct (WFD), ultra wideband (UWB), infrared data association (IrDA), Bluetooth low energy (BLE), near field communication (NFC), a radio frequency (RF) signal, and the like. For example, wired communication between elements of the examples described herein may be performed via a pair cable, a coaxial cable, an optical fiber cable, an Ethernet cable, and the like. Communication over the network can use a wide variety of communication protocols (e.g., TCP/IP, HTTP, SMTP, FTP), encodings or formats (e.g., HTML, XML), and/or protection schemes (e.g., VPN, secure HTTP, SSL).

The computing device 100 may be a smartphone, a smartwatch, a tablet, and the like, for example. The computing device 100 may include one or more processors 110, one or more memory devices 120, a biometric measurement application 130, an input device 140, a display device 150, an output device 160, one or more cameras 170, and one or more sensors 180. Each of the components of the computing device 100 may be operatively connected with one another via a system bus. For example, the system bus may be any of several types of bus structures that may further interconnect to a memory bus (with or without a memory controller), a peripheral bus, and/or a local bus using any of a variety of commercially available bus architectures.

The server computing system 300 may include one or more processors 310, one or more memory devices 320, and a biometric measurement application 330. Each of the components of the server computing system 300 may be operatively connected with one another via a system bus. For example, the system bus may be any of several types of bus structures that may further interconnect to a memory bus (with or without a memory controller), a peripheral bus, and/or a local bus using any of a variety of commercially available bus architectures.

The external computing device 400 may include similar features as the computing device 100 including one or more processors, one or more memory devices, a biometric measurement application 430, an input device, a display device, an output device, one or more cameras, and one or more sensors, and a detailed description of these features in the context of the external computing device 400 will be omitted for the sake of brevity. Each of the features of the external computing device 400 may be operatively connected with one another via a system bus. For example, the system bus may be any of several types of bus structures that may further interconnect to a memory bus (with or without a memory controller), a peripheral bus, and/or a local bus using any of a variety of commercially available bus architectures.

For example, the one or more processors 110, 310 can be any suitable processing device that can be included in a computing device 100 or in server computing system 300. For example, such a processor 110, 310 may include one or more of a processor, processor cores, a controller and an arithmetic logic unit, a central processing unit (CPU), a graphics processing unit (GPU), a digital signal processor (DSP), an image processor, a microcomputer, a field programmable array, a programmable logic unit, an application-specific integrated circuit (ASIC), a microprocessor, a microcontroller, etc., and combinations thereof, including any other device capable of responding to and executing instructions in a defined manner. The one or more processors 110, 310 can be a single processor or a plurality of processors that are operatively connected, for example in parallel.

The one or more memory devices 120, 320 can include one or more non-transitory computer-readable storage mediums, such as such as a Read Only Memory (ROM), Programmable Read Only Memory (PROM), Erasable Programmable Read Only Memory (EPROM), and flash memory, a USB drive, a volatile memory device such as a Random Access Memory (RAM), an internal or external hard disk drive (HDD), floppy disks, a blue-ray disk, or optical media such as CD ROM discs and DVDs, and combinations thereof. However, examples of the one or more memory devices 120, 320 are not limited to the above description, and the one or more memory devices 120, 320 may be realized by other various devices and structures as would be understood by those skilled in the art.

For example, the one or more memory devices 120 can store instructions, that when executed, cause the one or more processors 110 to obtain biometric information of a user associated with the computing device, to determine whether the user completes one or more biometric goals based on the biometric information, to receive, in response to a selection of a first user interface screen among a plurality of user interface screens, data associated with the first user interface screen and data associated with one or more first biometric achievement user interface screens, to provide, for presentation on a display device of the computing device, the first user interface screen as at least part of a home screen of the computing device; and to provide, for presentation on the display device, a corresponding first biometric achievement user interface screen associated with completion of a first biometric goal among the one or more biometric goals, in response to the user completing the first biometric goal, as described according to examples of the disclosure.

For example, the one or more memory devices 320 can store instructions, that when executed, cause the one or more processors 310 to receive from the computing device 100 or the external computing device 400, a request for data associated with a user interface screen, as described according to examples of the disclosure. For example, the one or more memory devices 320 can store instructions, that when executed, cause the one or more processors 310 to transmit the data associated with the user interface screen to the computing device 100 or the external computing device 400, in response to receiving the request, as described according to examples of the disclosure. For example, the one or more memory devices 320 can store instructions, that when executed, cause the one or more processors 310 to further transmit data associated with one or more biometric achievement user interface screens to the computing device 100 or the external computing device 400, in response to receiving the request, as described according to examples of the disclosure.

The one or more memory devices 120 can also include data 122 and instructions 124 that can be retrieved, manipulated, created, or stored by the one or more processors 110. In some examples, such data can be accessed and used as input to obtain and output the user interface screen and biometric achievement user interface screens, as described according to examples of the disclosure. The one or more memory devices 320 can also include data 322 and instructions 324 that can be retrieved, manipulated, created, or stored by the one or more processors 310. In some examples, such data can be accessed and used as input to obtain and output the user interface screen and biometric achievement user interface screens, as described according to examples of the disclosure.

The biometric measurement application 130 can include any biometric application which allows or is capable of allowing a user to measure biometric information of a user using the computing device 100. For example, the biometric measurement application 130 may be configured to enable a user to set or define biometric goals with respect to an activity that the user is to engage in, for example. The biometric measurement application 130 may be configured to enable a user to select a user interface screen from among a plurality of user interface screens which is displayable on the display device 150 of the computing device 100. The biometric measurement application 130 may be configured to provide, in response to the selection of the user interface screen, data associated with the user interface screen, as well as data associated with one or more biometric achievement user interface screens. That is, in conjunction with receiving data associated with the user interface screen (in response to the selection of the user interface screen), the computing device 100 also receives data associated with one or more biometric achievement user interface screens.

In some implementations, a user of the external computing device 400 may execute the biometric measurement application 430 to define biometric goals with respect to an activity that the user is to engage in, where the biometric measurement application 130 at the computing device 100 measures the biometrics of the user and determines whether a biometric goal and/or intermediate biometric goal has been achieved. In some implementations, a user of the computing device 100 may execute the biometric measurement application 130 to access a portal to the biometric measurement application 330 through which the user can perform various operations including selecting a user interface screen from among a plurality of user interface screens. In some implementations, a user of the external computing device 400 may execute the biometric measurement application 430 to access a portal to the biometric measurement application 330 through which the user can perform various operations including selecting a user interface screen from among a plurality of user interface screens, where data associated with the user interface screen can be transmitted to the computing device 100 together with data associated with one or more biometric achievement user interface screens or data associated with the user interface screen can be transmitted to the external computing device 400 together with data associated with one or more biometric achievement user interface screens.

The computing device 100 may include an input device 140 configured to receive an input from a user and may include, for example, one or more of a keyboard (e.g., a physical keyboard, virtual keyboard, etc.), a mouse, a joystick, a button, a switch, an electronic pen or stylus, a gesture recognition sensor (e.g., to recognize gestures of a user including movements of a body part), an input sound device or voice recognition sensor (e.g., a microphone to receive a voice command), a track ball, a remote controller, a portable (e.g., a cellular or smart) phone, and so on. The input device 140 may also be embodied by a touch-sensitive display device having a touchscreen capability, for example. The input device 140 may be used by a user of the computing device 100 to provide an input to select a user interface screen, to take a biometric measurement, to provide an input to execute the biometric measurement application 130, to define or select biometric goals, etc. For example, the input may be a voice input, a touch input, a gesture input, a click via a mouse or remote controller, and so on.

The computing device 100 includes a display device 150 which presents information viewable by the user, for example on a user interface (e.g., a graphical user interface). For example, the display device 150 may be a non-touch sensitive display. The display device 150 may include a liquid crystal display (LCD), a light emitting diode (LED) display, an organic light emitting diode (OLED) display, active matrix organic light emitting diode (AMOLED), flexible display, 3D display, a plasma display panel (PDP), a cathode ray tube (CRT) display, and the like, for example. However, the disclosure is not limited to these example display devices and may include other types of display devices.

The computing device 100 includes an output device 160 configured to provide an output to the user and may include, for example, one or more of an audio device (e.g., one or more speakers), a haptic device to provide haptic feedback to a user, a light source (e.g., one or more light sources such as LEDs which provide visual feedback to a user), and the like. For example, in some implementations of the disclosure the user may receive one or more of haptic feedback, visual feedback, and audio feedback in response to a biometric goal being completed and/or an intermediate goal being completed. The output device 160 may provide various indications to inform, alert, or notify the user to perform a certain action as part of the process for taking the biometric measurement.

The computing device 100 includes one or more cameras 170. For example, the one or more cameras 170 may include an imaging sensor (e.g., a complementary metal-oxide-semiconductor (CMOS) or charge-coupled device (CCD)) to capture, detect, or recognize a user's behavior, figure, expression, etc. In some implementations, the one or more cameras 170 may be used to detect (sense) biometric information about the user, for example, by capturing imagery of the user while the user engages in an activity.

The computing device 100 includes one or more sensors 180. For example, the one or more sensors 180 may include an inertial measurement unit 182 which includes one or more accelerometers 182a and/or one or more gyroscopes 182b. The one or more accelerometers 182a may be used to capture motion information with respect to the computing device 100 which may be used to obtain biometric information about the user. The one or more gyroscopes 182b may also be used additionally, or alternatively, to capture motion information with respect to the computing device 100.

For example, the one or more sensors 180 may include one or more activity detectors 184. For example, the one or more activity detectors 184 may include a first activity detector 184a configured to detect a first type of activity and a second activity detector 184b configured to detect a second type of activity. The one or more activity detectors 184 may be configured to track or determine a type of activity the user is engaging in. For example, the one or more activity detectors 184 may detect a start time and an end time of an activity and analyze data which is obtained by the one or more sensors 180, for example, to determine the type of activity according to known methods. For example, data output by the one or more sensors may indicate whether a user is running, swimming, or walking, and may indicate whether a user is stationary or moving (e.g., based on GPS data).

The one or more sensors 180 may also include other sensors such as a magnetometer, GPS sensor, strain gauge, and the like, to determine biometric information about the user, for example.

Figure 3:
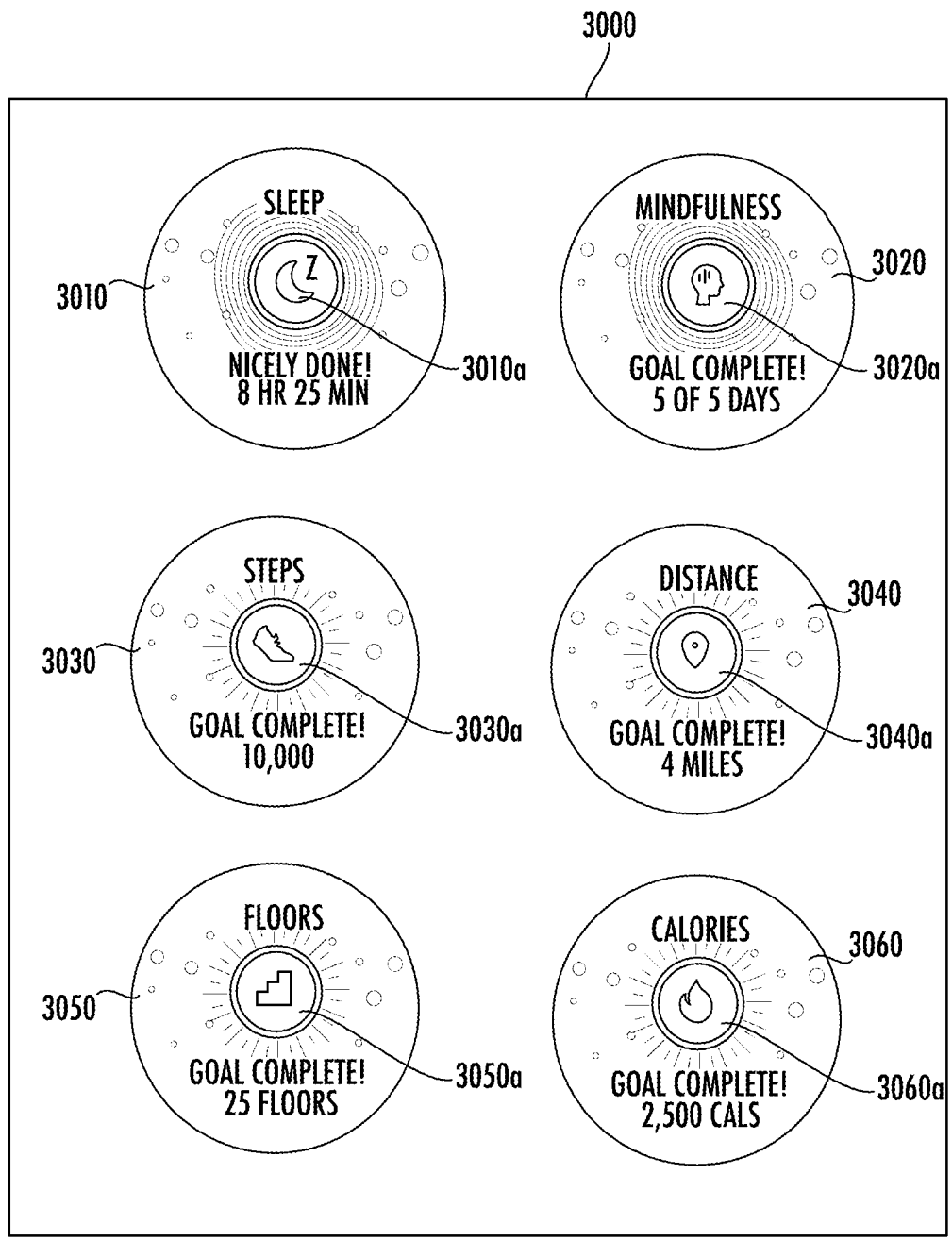
FIG. 3 is an example illustration of various default biometric achievement user interface screens of a computing device, according to one or more examples of the disclosure.

Referring to FIG. 3, an example illustration of various default biometric achievement user interface screens of a computing device is shown, according to one or more examples of the disclosure. In FIG. 3, various default biometric achievement user interface screens of the computing device 100 may be stored, for example in one or more memory devices 3000 (e.g., the one or more memory devices 120 of the computing device 100 or in the one or more memory devices 320 of the server computing system 300). Example default biometric achievement user interface screens may include a first default biometric achievement user interface screen 3010 relating to a sleep activity, a second default biometric achievement user interface screen 3020 relating to a mindfulness activity, a third default biometric achievement user interface screen 3030 relating to a number of steps taken by the user, a fourth default biometric achievement user interface screen 3040 relating to a distance traveled by the user, a fifth default biometric achievement user interface screen 3050 relating to a number of floors climbed by the user, and a sixth default biometric achievement user interface screen 3060 relating to a diet or nutrition activity (e.g., number of calories burned by the user). The first default biometric achievement user interface screen 3010 may include a first user interface element 3010*a* which denotes or is associated with the sleep activity, the second default biometric achievement user interface screen 3020 may include a second user interface element 3020*a* which denotes or is associated with the mindfulness activity, the third default biometric achievement user interface screen 3030 may include a third user interface element 3030*a* which denotes or is associated with the number of steps taken by the user, the fourth default biometric achievement user interface screen 3040 may include a fourth user interface element 3040*a* which denotes or is associated with the distance traveled by the user, the fifth default biometric achievement user interface screen 3050 may include a second user interface element 3050*a* which denotes or is associated with the number of floors climbed by the user, and the sixth default biometric achievement user interface screen 3060 may include a sixth user interface element 3060*a* which denotes or is associated with the diet or nutrition activity (e.g., number of calories burned by the user).

According to examples of the disclosure, the various default biometric achievement user interface screens of the computing device 100 may be deleted, overwritten, or altered, in response to a user selecting a user interface screen from among a plurality of user interface screens, and the computing device 100 receiving data associated with the selected user interface screen and data associated with one or more biometric achievement user interface screens. For example, in some implementations one or more user interface elements of a default biometric achievement user interface screen may be replaced by a user interface element derived from the selected user interface screen. For example, in some implementations the default biometric achievement user interface screen associated with a particular activity (e.g., the sleep activity) may be unmapped from or disassociated with the particular activity, and the biometric achievement user interface screen associated with the selected user interface screen may be mapped to or associated with the particular activity. In some implementations, the data corresponding to the default biometric achievement user interface screen associated with the particular activity may be deleted or overwritten. Deleting or overwriting the data associated with the original default biometric achievement user interface screen may conserve computing resources of the computing device 100, for example, storage resources relating to the one or more memory devices 120.

Figure 4A:
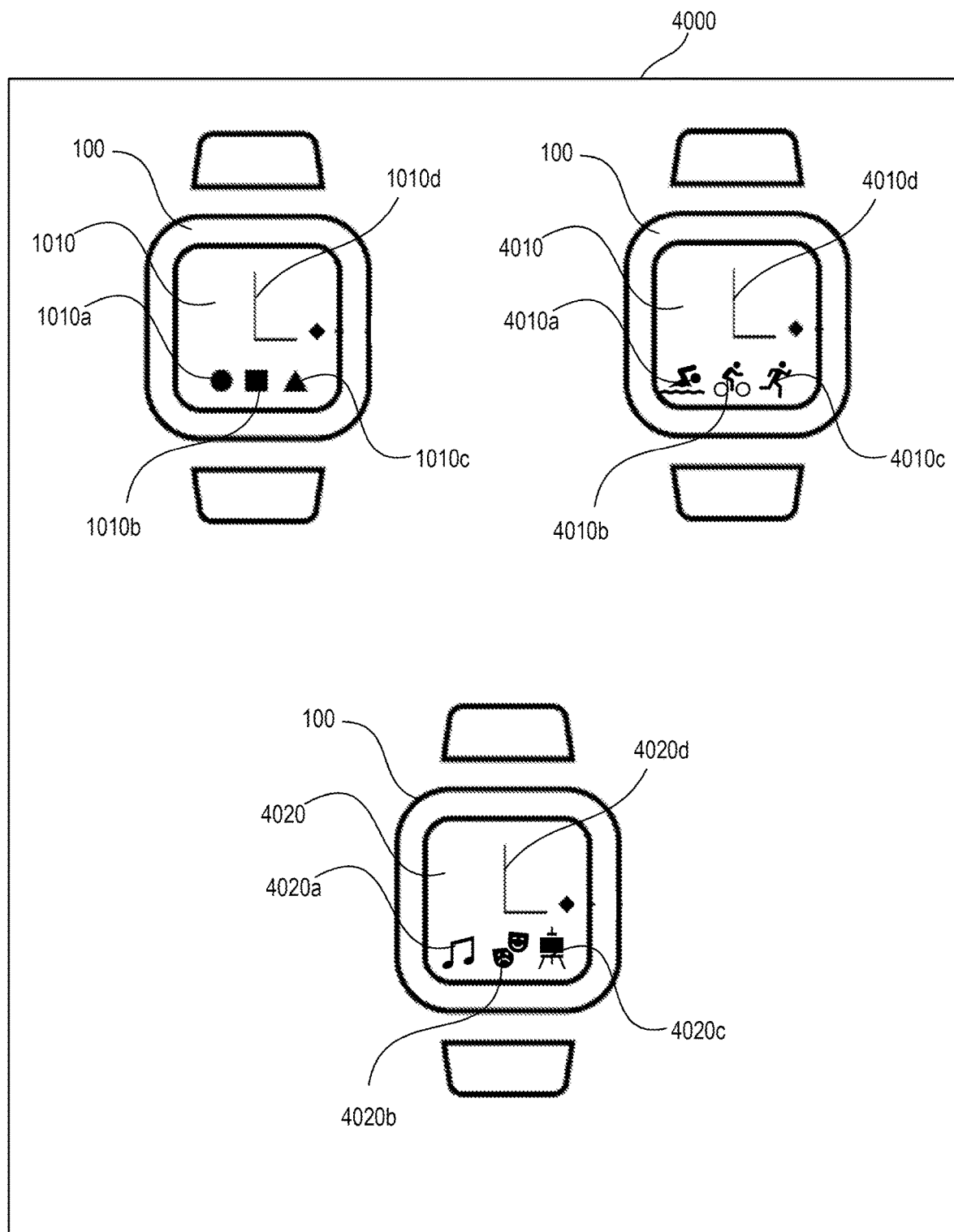
FIG. 4A is an example illustration of various user interface screens which can be selected for presentation on a computing device, according to one or more examples of the disclosure.

Referring to FIG. 4A, an example illustration of various user interface screens which can be selected for presentation on a computing device is shown, according to one or more examples of the disclosure. In FIG. 4A, an example user interface 4000 of the biometric measurement application is shown. For example, the user interface 4000 may be provided by any of biometric measurement applications 130, 330, or 430. For example, the user interface 4000 may be generated by any of user interface (UI) generators 130*b*, 330*b*, or 430*b*. User interface 4000 may display a plurality of user interface screens which are selectable by the user and which can be used at least in part as a home screen of the computing device 100. For example, the user interface screens may be in the form of a watch face. In FIG. 4A, the user interface screen 1010 is in the form of a watch face and includes various user interface elements, including first user interface element 1010*a* which is circle-shaped, second user interface element 1010*b* which is square-shaped, third user interface element 1010*c* which is triangle-shaped, and clock hands 1010*d* which can be used to indicate a time of day. User interface screen 4010 is in the form of a watch face and includes various user interface elements, including first user interface element 4010*a* which is a graphic image of a swimmer, second user interface element 4010*b* which is a graphic image of a cyclist, third user interface element 4010*c* which is a graphic image of a runner, and clock hands 4010*d* which can be used to indicate a time of day. User interface screen 4020 is in the form of a watch face and includes various user interface elements, including first user interface element 4020*a* which is a graphic image of a musical note, second user interface element 4020*b* which is a graphic image of theater masks, third user interface element 4020*c* which is a graphic image of an easel, and clock hands 4020*d* which can be used to indicate a time of day. Therefore, a user can select a user interface screen which appeals to the user and can be displayed on the computing device 100 at least as part of the home screen of the computing device 100. Furthermore, the user can indirectly customize a biometric achievement user interface screen via selection of the user interface screen. That is, in response to a selection of one of the user interface screens, data associated with not only the user interface screen is transmitted to the computing device 100 (e.g., from the server computing system 300 or external computing device 400), but also data associated with one or more biometric achievement user interface screens. Furthermore, the one or more biometric achievement user interface screens may include one or more user interface elements which are derived from or are the same as user interface elements which are provided in the user interface screen. Accordingly, if a user wants a biometric achievement user interface screen with a particular feature (e.g., a sport theme), the user can select a user interface screen having the same or similar feature (e.g., user interface screen 4010 having user interface elements involving sports). Likewise, if a user wants a biometric achievement user interface screen with a particular feature (e.g., an arts theme), the user can select a user interface screen having the same or similar feature (e.g., user interface screen 4020 having user interface elements involving the arts). Therefore, according to examples described herein the user does not specifically select the biometric achievement user interface screens, but instead selects a main or general user interface screen from which the biometric achievement user interface screens are derived. Accordingly, a number of interactions required of the user is reduced and network resources are conserved by the automatic transmission of the data associated with the one or more biometric achievement user interface screens, rather than a user navigating through various menus or applications to select specific biometric achievement user interface screens.

In some implementations, the computing device 100 may be configured to store more than one user interface screen in the one or more memory devices 120. For example, the user may select a plurality of user interface screens from among the plurality of user interface screens via any of the biometric measurement applications 130, 330, 430.

In some implementations, the user can switch between different user interface screens among the plurality of user interface screens by providing an input to the biometric measurement application 130. In other implementations, the biometric measurement application 130 may be configured to automatically switch between different user interface screens, for example, according to an activity being engaged in by the user as determined by the one or more activity detectors 184. That is, a first user interface screen may be switched to a second user interface screen, in response to the output provided by the one or more activity detectors 184 indicating the user has changed from performing a first activity to performing a second activity. For example, if the first activity detector 184*a* detects the user is engaged in a sporting activity (e.g., swimming), the user interface screen 4010 may be displayed as at least part of the home screen of the computing device 100. For example, if the second activity detector 184*b* subsequently detects the user is engaged in an artistic activity (e.g., playing piano), the biometric measurement application 130 may be configured to switch the user interface screen from the user interface screen 4010 to the user interface screen 4020 which is then displayed as at least part of the home screen of the computing device 100.

FIGS. 4B through 4C are example illustrations of various biometric achievement user interface screens which can be selected for presentation on a computing device, according to one or more examples of the disclosure. In some implementations, each of the biometric achievement user interface screens may include different user interface elements from the user interface screen to denote different biometric goals for different activities. For example, in FIG. 4A the user interface screen 4010 may include various graphic images (swimming, cycling, running). For example, in FIG. 4B the first biometric achievement user interface screen 4030 may include the swimming user interface element 4030*a*, the second biometric achievement user interface screen 4040 may include the cycling user interface element 4040*a*, and the third biometric achievement user interface screen 4050 may include the running user interface element 4050*a*. For example, the first biometric achievement user interface screen 4030 may be associated with a biometric goal relating to a first activity (e.g., swimming 20 laps), the second biometric achievement user interface screen 4040 may be associated with a biometric goal relating to a second activity (e.g., cycling 10 miles), and the third biometric achievement user interface screen 4050 may be associated with a biometric goal relating to a third activity (e.g., running 3 miles). The biometric achievement user interface screens may have some user interface elements in common. For example, user interface elements 4030*b*, 4040*b*, and 4050*b* may have a similar graphical design.

For example, the biometric measurement application 130 may be configured to automatically switch between different biometric achievement user interface screens, for example, according to the activity being engaged in by the user as determined by the one or more activity detectors 184. That is, a first biometric achievement user interface screen may be switched to a second biometric achievement user interface screen, in response to the output provided by the one or more activity detectors 184 indicating the user has changed from performing a first activity to performing a second activity and based on the biometric measurement application 130 determining biometric goals associated with the first and second activities have been achieved. For example, if the first activity detector 184*a* detects the user is engaged in a sporting activity (e.g., swimming) and the biometric measurement application 130 determines a biometric goal has been achieved (e.g., by swimming 20 laps), the first biometric achievement user interface screen 4030 may be displayed. For example, if the second activity detector 184*b* subsequently detects the user is engaged in a cycling activity (e.g., riding a bicycle) and the biometric measurement application 130 determines a biometric goal has been achieved (e.g., by cycling 10 miles), the biometric measurement application 130 may be configured to switch the biometric achievement user interface screen from the first biometric achievement user interface screen 4030 to the second biometric achievement user interface screen 4040.

In some implementations, each of the biometric achievement user interface screens may include different user interface elements from the user interface screen to denote different biometric goals for a same activity. For example, in FIG. 4A the user interface screen 4020 may include various graphic images (musical note, theater masks, and an art easel). For example, in FIG. 4C the first biometric achievement user interface screen 4060 may include the musical note user interface element 4060*a*, the second biometric achievement user interface screen 4070 may include the theater masks user interface element 4070*a*, and the third biometric achievement user interface screen 4080 may include the art easel user interface element 4080*a*. For example, the first biometric achievement user interface screen 4060 may be associated with an intermediate biometric goal relating to a first activity (e.g., practicing piano for 20 minutes), the second biometric achievement user interface screen 4070 may be associated with another intermediate biometric goal relating to the first activity (e.g., practicing piano for 40 minutes), and the third biometric achievement user interface screen 4080 may be associated with the completion of the biometric goal relating to the first activity (e.g., practicing piano for one hour). The biometric achievement user interface screens may have some user interface elements in common. For example, user interface elements 4060*b*, 4070*b*, and 4080*b* may have a similar graphical design.

In some implementations, a user interface element provided in the biometric achievement user interface screen is the same as a user interface element provided in the user interface screen. For example, the graphic image of the swimmer corresponding to user interface element 4010*a* from FIG. 4A may be the same as the graphic image of the swimmer corresponding to user interface element 4030*a* from FIG. 4B. However, in some implementations, the user interface element provided in the biometric achievement user interface screen may be a derivation or variation of the user interface element provided in the user interface screen (e.g., having a same genre or design feature). For example, the user interface element 4030*a* from FIG. 4B may instead be a graphic image of a wave instead of the graphic image of the swimmer corresponding to user interface element 4010*a* from FIG. 4A. Likewise, the user interface element provided in the biometric achievement user interface screen may have the same color as the user interface element provided in the user interface screen, or the colors may be different from each other.

Referring to FIGS. 5A-5D, example illustrations including various flow diagrams for a computing device to obtain data associated with user interface screens and data associated with biometric achievement user interface screens is shown, according to one or more examples of the disclosure.

Figure 5A:
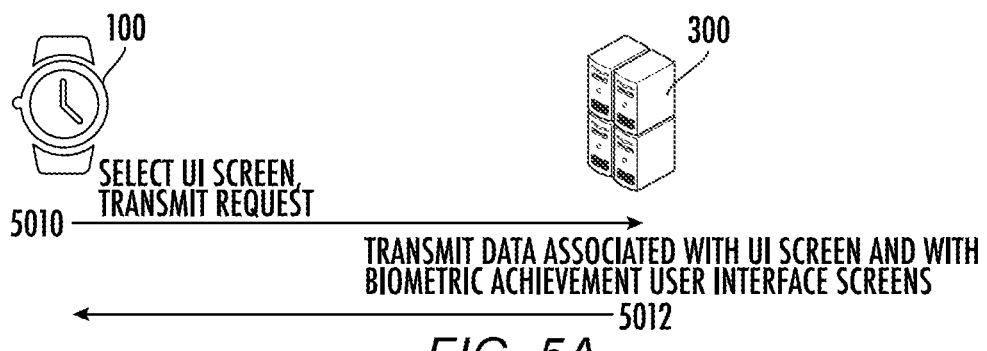
FIGS. 5A through 5D are example illustrations including various flow diagrams for a computing device to obtain data associated with user interface screens and data associated with biometric achievement user interface screens, according to one or more examples of the disclosure.

For example, in FIG. 5A, at 5010 the user can select, via the biometric measurement application 130 at the computing device 100, a user interface screen from a plurality of user interface screens which are stored remotely, for example, at a server computing system 300. In response to the user selecting the user interface screen at the computing device 100, at 5010 a request can then be transmitted from the computing device 100 to the server computing system 300. In response to the server computing system 300 receiving the request from the computing device 100, at 5012 the server computing system 300 can transmit data associated with the user interface screen to the computing device 100. Furthermore, the server computing system 300 can automatically transmit data associated with one or more biometric achievement user interface screens to the computing device 100. For example, each of the one or more biometric achievement user interface screens may include one or more user interface elements from the selected user interface screen and each of the one or more biometric achievement user interface screens may be associated with various biometric goals for various activities.

Figure 5B:
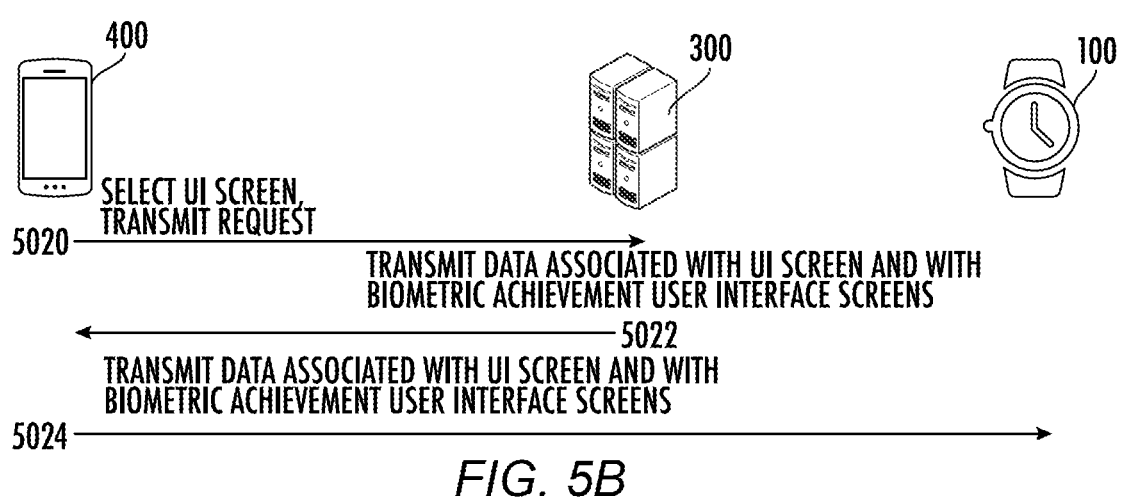

In FIG. 5B, at 5020 the user can select, via the biometric measurement application 430 at the external computing device 400, the user interface screen from a plurality of user interface screens which are stored remotely, for example, at the server computing system 300. In response to the user selecting the user interface screen at the external computing device 400, at 5020 a request can then be transmitted from the external computing device 400 to the server computing system 300. In response to the server computing system 300 receiving the request from the external computing device 400, at 5022 the server computing system 300 can transmit data associated with the user interface screen and data associated with one or more biometric achievement user interface screens, to the external computing device 400. At 5024, in response to receiving the data associated with the user interface screen and the data associated with one or more biometric achievement user interface screens, the external computing device 400 transmits the data associated with the user interface screen to the computing device and the data associated with one or more biometric achievement user interface screens to the computing device 100. For example, each of the one or more biometric achievement user interface screens may include one or more user interface elements from the selected user interface screen and each of the one or more biometric achievement user interface screens may be associated with various biometric goals and activities, as already discussed above. For example, the external computing device 400 may be a smartphone and the computing device 100 may be a smartwatch.

Figure 5C:
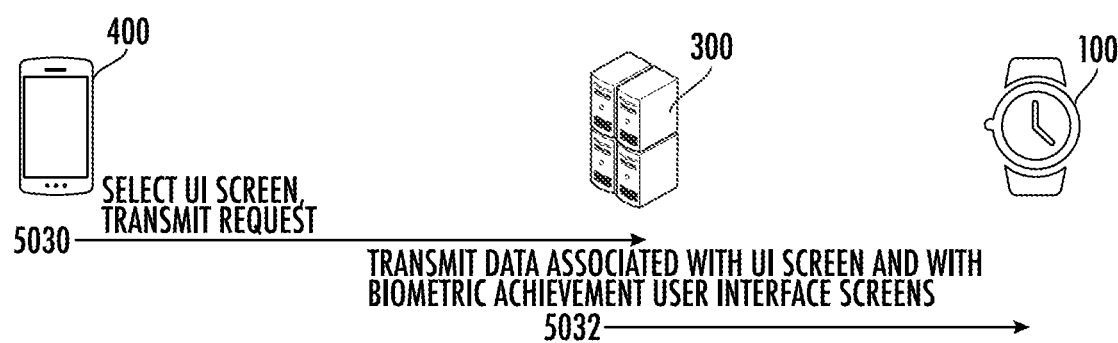

In FIG. 5C, at 5030 the user can select, via the biometric measurement application 430 at the external computing device 400, the user interface screen from a plurality of user interface screens which are stored remotely, for example, at the server computing system 300. In response to the user selecting the user interface screen at the external computing device 400, at 5030 a request can then be transmitted from the external computing device 400 to the server computing system 300. In response to the server computing system 300 receiving the request from the external computing device 400, at 5032 the server computing system 300 can transmit data associated with the user interface screen and data associated with one or more biometric achievement user interface screens, to the computing device 100. For example, the request transmitted from the external computing device 400 at 5030 may include identification information (e.g., an International Mobile Station Equipment Identity number, an International Mobile Subscriber Identity number, an International Mobile Equipment Identity number, manufacturer information, port information, etc.) regarding the computing device 100 so that the server computing system 300 knows which computing device is to receive the data associated with the user interface screen and data associated with one or more biometric achievement user interface screens. For example, each of the one or more biometric achievement user interface screens may include one or more user interface elements from the selected user interface screen and each of the one or more biometric achievement user interface screens may be associated with various biometric goals and activities, as already discussed above. For example, the external computing device 400 may be a smartphone and the computing device 100 may be a smartwatch.

Figure 5D:
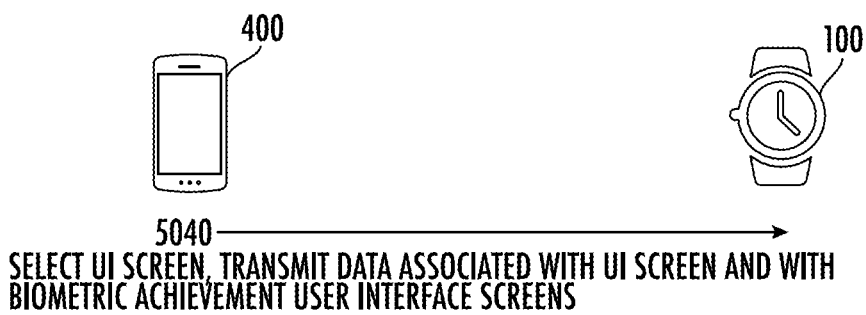

In FIG. 5D, at 5040, the user can select, via a biometric measurement application 430 at an external computing device 400, the user interface screen from a plurality of user interface screens which are stored locally on the external computing device 400. In response to the user selecting the user interface screen at the external computing device 400, at 5040 the external computing device 400 can transmit data associated with the user interface screen to the computing device 100. Furthermore, the external computing device 400 can automatically transmit data associated with one or more biometric achievement user interface screens to the computing device 100. For example, each of the one or more biometric achievement user interface screens may include one or more user interface elements from the selected user interface screen and each of the one or more biometric achievement user interface screens may be associated with various biometric goals and activities, as already discussed above. For example, the external computing device may be a smartphone and the computing device may be a smartwatch.

Figure 6:
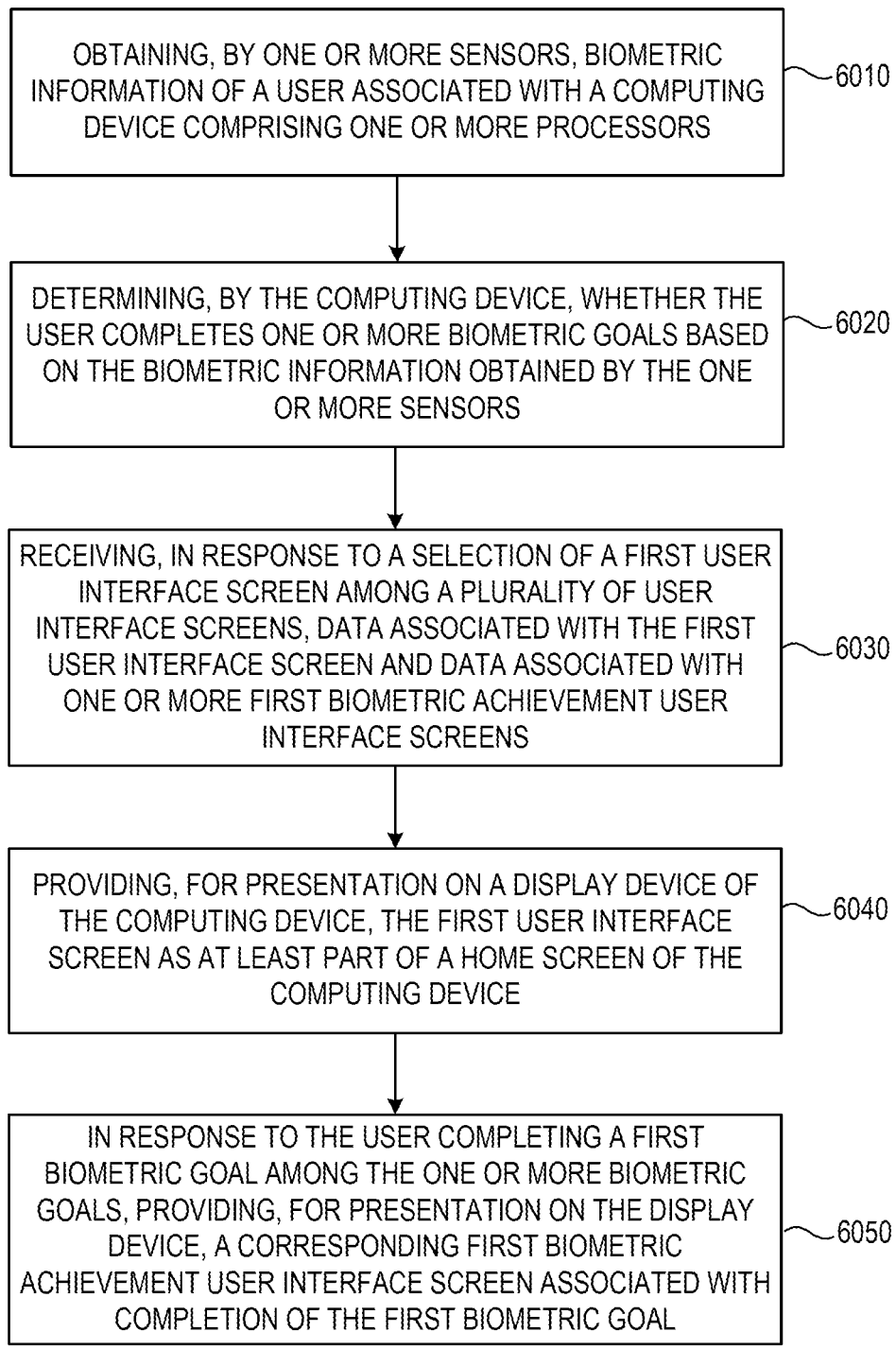
FIG. 6 is a flow diagram of an example, non-limiting computer-implemented method according to one or more examples of the disclosure.

Referring to FIG. 6, a flow diagram of an example, non-limiting computer-implemented method according to one or more examples of the disclosure. The flow diagram FIG. 6 illustrates a method 6000 for providing biometric achievement user interface screens relating to a user interface screen selected by a user.

At 6010, the method includes obtaining, by one or more sensors, biometric information of a user associated with a computing device comprising one or more processors. For example, various sensors from among sensors 180 may be configured to detect or sense biometric information of a user while the user engages in an activity.

At 6020, the method includes determining, by the computing device, whether the user completes one or more biometric goals based on the biometric information obtained by the one or more sensors. For example, computing device 100 may be configured to store various biometric goals relating to various activities in the one or more memory devices 120, the one or more memory devices 320, or in one or more memory devices of the external computing device 400. For example, the computing device 100 (e.g., via biometric measurement application 130) may be configured to track the progress of a user (e.g., via biometric goal tracker 130*a*) as the user engages in an activity and determine whether the user completes a biometric goal (e.g., walking a certain number of steps, cycling a certain number of miles, swimming a certain number of laps, sleeping a certain number of hours, etc.). In some implementations, biometric information of the user may be transmitted to external computing device 400 and/or server computing system 300 where the biometric goal tracker 430*a* and/or biometric goal tracker 330*a* can track the progress of the user as the user engages in an activity and determine whether the user completes a biometric goal.

For example, the user may define or select one or more goals associated with an activity through the biometric measurement application 130 (or the biometric measurement application 130 may have one or more default biometric goals associated with the activity). When the user achieves a goal, a celebration may be displayed on a biometric achievement user interface screen of the display device 150. In some implementations, an intermediate celebration (or micro-celebration) may be displayed on the biometric achievement user interface screen of the display device 150 at one or more predetermined points before the biometric goal is actually achieved which correspond to the threshold values (intermediate goals) described above. Different celebrations may also be shown according to a type of activity. The celebrations may include a graphical image that is displayed and intended to encourage the user with respect to achieving their biometric goal which is associated with the activity. The celebrations may include an animation including a series of graphical images that are displayed and intended to encourage the user with respect to achieving their biometric goal which is associated with the activity. Haptic feedback and/or audio output may also be provided via output device 160 in relation to completing a biometric goal and/or achieving an intermediate biometric goal.

The particular biometric achievement user interface screen which may be shown may be dependent on the user interface screen which is displayed as part of the home screen of the computing device 100. A user may select the user interface screen as discussed above. For example, at 6030, the method includes receiving, in response to a selection of a first user interface screen among a plurality of user interface screens, data associated with the first user interface screen and data associated with one or more first biometric achievement user interface screens. For example, the computing device 100 may receive the data associated with the first user interface screen and data associated with one or more first biometric achievement user interface screens in accordance with the examples discussed above with respect to FIGS. 5A-5D.

At 6040, the method includes providing, for presentation on a display device of the computing device, the first user interface screen as at least part of a home screen of the computing device. For example, the first user interface screen may correspond to a watch face for a wearable computing device (e.g., a smartwatch).

At 6050, the method includes in response to the user completing a first biometric goal among the one or more biometric goals, providing, for presentation on the display device, a corresponding first biometric achievement user interface screen associated with completion of the first biometric goal. For example, the biometric measurement application 130 may be configured to limit a physical area which a biometric achievement user interface screen encompasses on the display device 150, for example, to save power of the computing device 100 (e.g., for powering the display of the display device 150). The biometric measurement application 130 may limit the physical area of the biometric achievement user interface screen to a threshold area value (e.g., ¼ of an area of the displayable surface of the display device 150, ½ of an area of the displayable surface of the display device 150, ⅔ of an area of the displayable surface of the display device 150, etc.). In some implementations, the biometric measurement application 130 may additionally, or alternatively, limit a duration for which the biometric achievement user interface screen is shown on the display device 150, for example, to save power of the computing device (e.g., for powering the display of the display device 150). The biometric measurement application 130 may limit the duration of time the biometric achievement user interface screen is shown to a threshold time value (e.g., less than 5 seconds, less than 3 seconds, less than 2 seconds, etc.). For example, the biometric achievement user interface screen may include an animation which celebrates the completion of a biometric goal or an intermediate biometric goal. The biometric measurement application 130 may also limit the duration of time the animation is shown to a threshold time value (e.g., less than 5 seconds, less than 3 seconds, less than 2 seconds, etc.). Upon expiration of the duration of time the biometric achievement user interface screen is shown, the biometric measurement application 130 may be configured to then display the home screen or display an altered home screen which includes some indication of the progress regarding the biometric goal.

Aspects of the above-described example embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM disks, Blue-Ray disks, and DVDs; magneto-optical media such as optical discs; and other hardware devices that are specially configured to store and perform program instructions, such as semiconductor memory, read-only memory (ROM), random access memory (RAM), flash memory, USB memory, and the like. Examples of program instructions include both machine code, such as produced by a compiler, and files containing higher level code that may be executed by the computer using an interpreter. The program instructions may be executed by one or more processors. The described hardware devices may be configured to act as one or more software modules in order to perform the operations of the above-described embodiments, or vice versa. In addition, a non-transitory computer-readable storage medium may be distributed among computer systems connected through a network and computer-readable codes or program instructions may be stored and executed in a decentralized manner. In addition, the non-transitory computer-readable storage media may also be embodied in at least one application specific integrated circuit (ASIC) or Field Programmable Gate Array (FPGA).

Each block of the flowchart illustrations may represent a unit, module, segment, or portion of code, which comprises one or more executable instructions for implementing the specified logical function(s). It should also be noted that in some alternative implementations, the functions noted in the blocks may occur out of order. For example, two blocks shown in succession may in fact be executed substantially concurrently (simultaneously) or the blocks may sometimes be executed in the reverse order, depending upon the functionality involved.

While the disclosure has been described with respect to various example embodiments, each example is provided by way of explanation, not limitation of the disclosure. Those skilled in the art, upon attaining an understanding of the foregoing, can readily produce alterations to, variations of, and equivalents to such embodiments. Accordingly, the disclosure does not preclude inclusion of such modifications, variations and/or additions to the disclosed subject matter as would be readily apparent to one of ordinary skill in the art. For example, features illustrated or described as part of one embodiment can be used with another embodiment to yield a still further embodiment. Thus, it is intended that the disclosure covers such alterations, variations, and equivalents.

What is claimed is:

1. A computing device, comprising:
   a display device;
   one or more sensors configured to obtain biometric information of a user associated with the computing device;

one or more memories configured to store instructions; and one or more processors configured to execute the instructions stored in the one or more memories to:
provide a selection of a first user interface screen among a plurality of user interface screens via a user input,
in response to providing the selection of the first user interface screen among the plurality of user interface screens, receive, from an external computing device, data associated with the first user interface screen and data associated with one or more first biometric achievement user interface screens, each of the one or more first biometric achievement user interface screens including one or more first user interface elements from the first user interface screen and each of the one or more first biometric achievement user interface screens being associated with respective biometric goals which are associated with activities of the user,
determine whether the user completes a first biometric goal associated with a first activity based on the biometric information obtained by the one or more sensors, and
in response to determining the user has completed the first biometric goal associated with the first activity, provide, for presentation on the display device, a corresponding first biometric achievement user interface screen associated with completion of the first biometric goal, the corresponding first biometric achievement user interface screen including one or more first user interface elements from the first user interface screen.

2. The computing device of claim 1, wherein the selection of the first user interface screen among the plurality of user interface screens is received at another external computing device.

3. The computing device of claim 1, wherein each of the one or more first biometric achievement user interface screens include different user interface elements from the first user interface screen to denote respective biometric goals among the one or more biometric goals.

4. The computing device of claim 1, wherein
the computing device is a wearable computing device, and
the first user interface screen corresponds to a watch face which is displayed on a home screen of the wearable computing device.

5. The computing device of claim 1, wherein in response to the user completing the first biometric goal among the one or more biometric goals, the one or more processors are configured to execute the instructions stored in the one or more memories to provide at least one of haptic feedback associated with the first biometric goal or an audio output associated with the first biometric goal.

6. The computing device of claim 1, wherein the one or more processors are configured to execute the instructions stored in the one or more memories to:
provide a selection of a second user interface screen among the plurality of user interface screens via the user input, and
in response to receiving the selection of the second user interface screen among the plurality of user interface screens via the user input, receive, from the external computing device, data associated with the second user interface screen and data associated with one or more second biometric achievement user interface screens,
wherein each of the one or more second biometric achievement user interface screens include one or more second user interface elements from the second user interface screen and each of the one or more second biometric achievement user interface screens are associated with respective biometric goals among the one or more biometric goals.

7. The computing device of claim 6, further comprising an activity detector configured to provide an output indicating an activity the user is performing among a plurality of activities,
wherein
the first user interface screen is associated with a first activity among the plurality of activities,
the second user interface screen is associated with a second activity among the plurality of activities, and
the one or more processors are configured to execute the instructions stored in the one or more memories to switch from providing, for presentation on the display device, the first user interface screen to providing, for presentation on the display device, the second user interface screen, in response to the output provided by the activity detector indicating the user has changed from performing the first activity to performing the second activity.

8. The computing device of claim 7, wherein the plurality of activities include two or more of walking, running, swimming, cycling, climbing, weightlifting, nutritional, or sleeping.

9. The computing device of claim 1, wherein
the first user interface screen is associated with a first activity among a plurality of activities,
the first biometric goal relates to the first activity,
the one or more first biometric achievement user interface screens are associated with achieving one or more thresholds toward the completion of the first biometric goal relating to the first activity, and
the corresponding biometric achievement user interface screen is associated with the completion of the first biometric goal relating to the first activity.

10. The computing device of claim 1, wherein
the one or more first user interface elements correspond to graphical images, and
the one or more processors are configured to execute the instructions stored in the one or more memories to limit an area which each of the first biometric achievement user interface screens encompass on the display device to less than a threshold size.

11. The computing device of claim 10, wherein the one or more processors are configured to execute the instructions stored in the one or more memories to provide an animation including the one or more first user interface elements, via one or more of the first biometric achievement user interface screens, and to limit a duration of time which the animation plays to less than a threshold duration of time.

12. The computing device of claim 1, wherein
before receiving the data associated with the corresponding biometric achievement user interface screen, the one or more processors are configured to execute the instructions stored in the one or more memories to provide, for presentation on the display device, a default biometric achievement user interface screen associated with the completion of the first biometric goal, data associated with the default biometric achievement user interface screen being stored in the one or more memories, and in response to receiving the data associated with the corresponding biometric achievement user interface screen, the one or more processors are configured to execute the instructions stored in the one or more memories to stop providing, for presentation on the display device, the default biometric achievement user interface screen associated with the completion of the first biometric goal.

13. The computing device of claim 1, wherein before receiving the data associated with the corresponding biometric achievement user interface screen, the one or more processors are configured to execute the instructions stored in the one or more memories to provide, for presentation on the display device, a default biometric achievement user interface screen associated with the completion of the first biometric goal, data associated with the default biometric achievement user interface screen being stored in the one or more memories, and in response to receiving the data associated with the corresponding biometric achievement user interface screen, the one or more processors are configured to execute the instructions stored in the one or more memories to delete the data associated with the default biometric achievement user interface screen or to overwrite the data associated with the default biometric achievement user interface screen with the data associated with the corresponding biometric achievement user interface screen.

14. The computing device of claim 1, wherein the first user interface screen is associated with a first activity among a plurality of activities, the first biometric goal relates to the first activity, before receiving the data associated with the one or more first biometric achievement user interface screens, the first biometric goal relating to the first activity is unmapped to any biometric achievement user interface screen, in response to receiving the data associated with the corresponding biometric achievement user interface screen, the one or more processors are configured to execute the instructions stored in the one or more memories to map the corresponding biometric achievement user interface screen to the first biometric goal to associate the corresponding biometric achievement user interface screen with the completion of the first biometric goal, and in response to the user completing the first biometric goal relating to the first activity the one or more processors are configured to execute the instructions stored in the one or more memories to provide, for presentation on the display device, the corresponding biometric achievement user interface screen associated with the completion of the first biometric goal.

15. A computer-implemented method, comprising:

providing, via a computing device, a selection of a first user interface screen among a plurality of user interface screens via a user input;

in response to providing the selection of the first user interface screen among the plurality of user interface screens, receiving, from an external computing device, data associated with the first user interface screen and data associated with one or more first biometric achievement user interface screens, each of the one or more first biometric achievement user interface screens including one or more first user interface elements from the first user interface screen and each of the one or more first biometric achievement user interface screens being associated with respective biometric goals among the one or more biometric goals which are associated with activities of the user, determining, based on biometric information obtained by one or more sensors of the computing device, whether the user completes a first biometric goal associated with a first activity; and in response to determining the user has completed the first biometric goal among associated with the first activity, providing, for presentation on a display device of the computing device, a corresponding first biometric achievement user interface screen associated with completion of the first biometric goal, the corresponding first biometric achievement user interface screen including one or more first user interface elements from the first user interface screen.

16. The computer-implemented method of claim 15, wherein each of the one or more first biometric achievement user interface screens include different user interface elements from the first user interface screen to denote respective biometric goals among the one or more biometric goals.

17. The computer-implemented method of claim 15, further comprising:

providing, by an activity detector, an output indicating an activity the user is performing among a plurality of activities, the plurality of activities including a first activity associated with the first user interface screen and a second activity associated with a second user interface screen; and switching from providing, for presentation on the display device, the first user interface screen to providing, for presentation on the display device, the second user interface screen, in response to the output provided by the activity detector indicating the user has changed from performing the first activity to performing the second activity.

18. A non-transitory computer-readable medium storing instructions which, when executed by one or more processors of a computing device, cause the one or more processors to perform operations, the operations comprising:

providing a selection of a first user interface screen among a plurality of user interface screens via a user input;

in response to providing the selection of the first user interface screen among the plurality of user interface screens, receiving, from an external computing device, data associated with the first user interface screen and data associated with one or more first biometric achievement user interface screens, each of the one or more first biometric achievement user interface screens including one or more first user interface elements from the first user interface screen and each of the one or more first biometric achievement user interface screens being associated with respective biometric goals among the one or more biometric goals which are associated with activities of the user;

determining, based on biometric information obtained by one or more sensors of the computing device, whether the user completes a first biometric goal associated with a first activity; and in response to determining the user has completed the first biometric goal among associated with the first activity, providing, for presentation on a display device of the computing device, a corresponding first biometric achievement user interface screen associated with completion of the first biometric goal, the corresponding first biometric achievement user interface screen including one or more first user interface elements from the first user interface screen.

19. The non-transitory computer-readable medium of claim 18, wherein the operations further comprise:
before receiving the data associated with the corresponding biometric achievement user interface screen, providing, for presentation on the display device, a default biometric achievement user interface screen associated with the completion of the first biometric goal, data associated with the default biometric achievement user interface screen being stored in the non-transitory computer-readable medium; and
in response to receiving the data associated with the corresponding biometric achievement user interface screen, deleting the data associated with the default biometric achievement user interface screen or overwriting the data associated with the default biometric achievement user interface screen with the data associated with the corresponding biometric achievement user interface screen.

20. The non-transitory computer-readable medium of claim 18, wherein
the first user interface screen is associated with a first activity among a plurality of activities,
the first biometric goal relates to the first activity,
before receiving the data associated with the one or more first biometric achievement user interface screens, the first biometric goal relating to the first activity is unmapped to any biometric achievement user interface screen,
in response to receiving the data associated with the corresponding biometric achievement user interface screen, the operations further comprise mapping the corresponding biometric achievement user interface screen to the first biometric goal to associate the corresponding biometric achievement user interface screen with the completion of the first biometric goal, and
in response to the user completing the first biometric goal relating to the first activity the operations comprise providing, for presentation on the display device, the corresponding biometric achievement user interface screen associated with the completion of the first biometric goal.

* * * * *